United States Patent
Jensen et al.

(10) Patent No.: US 9,119,586 B2
(45) Date of Patent: Sep. 1, 2015

(54) ULTRASOUND IMAGING SYSTEM

(75) Inventors: Ole Christian Jensen, Værløse (DK);
Johannes Anders Smith, Hellerup (DK); Kaj E Dunkan, Stenlille (DK); Torben Svanberg Nielsen, København S (DK)

(73) Assignee: B-K Medical Aps, Herlev (DK)

( * ) Notice: Subject to any disclaimer, the term of this patent is extended or adjusted under 35 U.S.C. 154(b) by 404 days.

(21) Appl. No.: 13/106,127

(22) Filed: May 12, 2011

(65) Prior Publication Data

US 2012/0289828 A1    Nov. 15, 2012

(51) Int. Cl.
*A61B 8/00* (2006.01)

(52) U.S. Cl.
CPC ............... *A61B 8/4405* (2013.01); *A61B 8/463* (2013.01); *A61B 8/467* (2013.01)

(58) Field of Classification Search
USPC .......... 600/407, 437–475; 715/700, 716–722, 715/764–807, 810–862
See application file for complete search history.

(56) References Cited

U.S. PATENT DOCUMENTS

| | | | |
|---|---|---|---|
| D626,235 S | 10/2010 | Smith et al. | |
| 2008/0132789 A1* | 6/2008 | Malchow et al. | 600/443 |
| 2010/0056912 A1* | 3/2010 | Urness et al. | 600/437 |

OTHER PUBLICATIONS

GE Healthcare, Venue The vision of point-of-care ultrasound, brochure, 2009, 8 sheets, www.venue.gehealthcare.com.
Esaote, Arm-held, the wearable ultrasound MyLabOne, brochure, Jan. 12, 2009, pp. 1-6, www.esaote.com.
Hitachi, HI Vision Preirus, brochure, Feb. 2009, pp. 1-6, www.hitachi-medical-systems.com.
Toshiba, Viamo performance to go, brochure, Nov. 2009, pp. 1-11, www.toshibamedicalsystems.com.
Esaote North America, MyLabOne, brochure, downloaded on May 12, 2011, 1 sheet, www.esaoteusa.com.
Esaote UK, MyLabOne, brochure, 2011, 1 sheet, www.esaote.co.uk.

* cited by examiner

*Primary Examiner* — Mark Remaly
(74) *Attorney, Agent, or Firm* — Anthony M. Del Zoppo, III; Driggs, Hogg, Daugherty & Del Zoppo, Co., LPA

(57) ABSTRACT

An ultrasound imaging system includes a console and a key pad. The console includes a two dimensional display region having a vertical dimension and a horizontal dimension, wherein the horizontal dimension is smaller than the vertical dimension. The display region includes an upper portion configured to display image data and a lower portion configured to display, concurrently with displaying the image data in the upper portion, a touch screen menu including a set of soft controls that are respectively configured to control a secondary set of ultrasound imaging functions. The key pad includes a set of physical controls that are respectively configured to control a primary set of ultrasound imaging functions, wherein the key pad has a width that is less than a width of the console. In one embodiment, the key pad is hermetically sealed, and is easily cleanable, disinfectable and/or sterilizable.

22 Claims, 5 Drawing Sheets

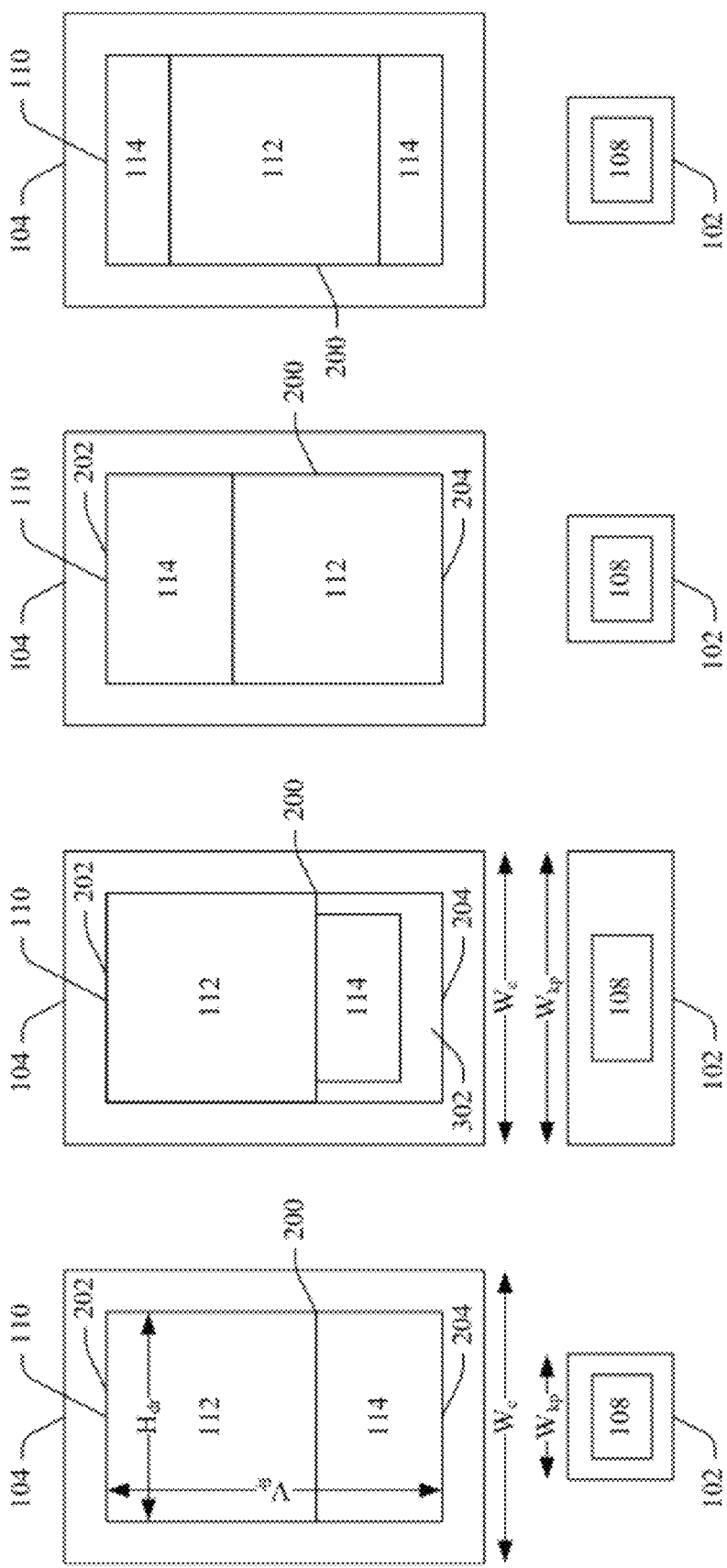

ULTRASOUND IMAGING SYSTEM

TECHNICAL FIELD

The following generally relates to ultrasound imaging and more particularly to a console and key pad of an ultrasound imaging system.

BACKGROUND

Ultrasound scanners provide useful information about the interior characteristics of an object under examination. In medical applications, clinicians have used ultrasound scanners to examine human subjects in settings such as hospitals, physician's offices, and other locations. Ultrasound scanners have been alternately used in the emergency room, operating room, radiology department, patient room, and similar environments. As such, it is sometimes desirable to transport the scanner from room-to-room. To this end, ultrasound scanners have been equipped with wheeled carts that allow the scanner to be rolled along the floor.

In a typical environment, a user of the scanner places the transducer on the body over the tissue of interest and begins scanning A monitor displays the information sensed by the transducer. The user may desire to change scanner parameters or settings, or determine a characteristic about the displayed information. For example, the user may want to increase the gain, adjust depth, change the zoom factor, etc. Such actions have required user interaction with a keyboard of the ultrasound scanner. For example, a conventional ultrasound scanner has included a keyboard with twenty or more keys, and the user activates a corresponding key to invoke a desired function.

Unfortunately, with twenty or more keys, it may not be readily convenient or easy for the user to locate and activate the key for the desired function. Furthermore, in such environments, the scanner may also come into contact with bodily fluids, which may get on and/or between keyboard keys, making it more difficult to clean the system after the procedure. Applications for these scanners may also place a premium on size. For example, in an operating room, space is often at a premium. Unfortunately, keyboards with twenty or more keys can be wider than the monitor, making the footprint of the system wider than needed to view images.

SUMMARY

Aspects of the application address the above matters, and others.

In one aspect, an ultrasound imaging system includes a console and a key pad. The console includes a two dimensional display region having a vertical dimension and a horizontal dimension, wherein the horizontal dimension is smaller than the vertical dimension. The display region includes an upper portion configured to display image data and a lower portion configured to display, concurrently with displaying the image data in the upper portion, a touch screen menu including a set of soft controls that are respectively configured to control a secondary set of ultrasound imaging functions. The key pad includes a set of physical controls that are respectively configured to control a primary set of ultrasound imaging functions, wherein the key pad has a width that is less than a width of the console.

In another aspect, an ultrasound imaging system includes a console with a display region arranged in a portrait orientation, wherein the display region concurrently presents ultrasound image data generated by the system and a set of soft secondary ultrasound imaging controls in different portions of the display region. The system further includes a key pad including a set of primary ultrasound imaging controls. The system further includes an interface configured to electrically communicate with a complementary interface of an ultrasound transducer.

In another aspect, a method includes concurrently displaying ultrasound image data and a set of soft controls vertically with respect to each other in a same display region of a console of an ultrasound imaging system, wherein a set of physical controls are part of a key pad of the ultrasound imaging system, which is narrower than the console of the ultrasound imaging system.

Those skilled in the art will recognize still other aspects of the present application upon reading and understanding the attached description.

BRIEF DESCRIPTION OF THE DRAWINGS

The application is illustrated by way of example and not limitation in the figures of the accompanying drawings, in which like references indicate similar elements and in which:

FIG. 2 illustrates an example display region of the console in which a set of soft controls is visually presented below image data;

FIG. 3 illustrates an example display region of the console in which at least one of image data or a set of soft controls is scalable and/or positionable within the display region;

FIG. 4 illustrates an example display region of the console in which a set of soft controls is presented above image data;

FIG. 5 illustrates an example display region of the console in which image data is presented between two sets of soft controls;

DETAILED DESCRIPTION

Figure 1:
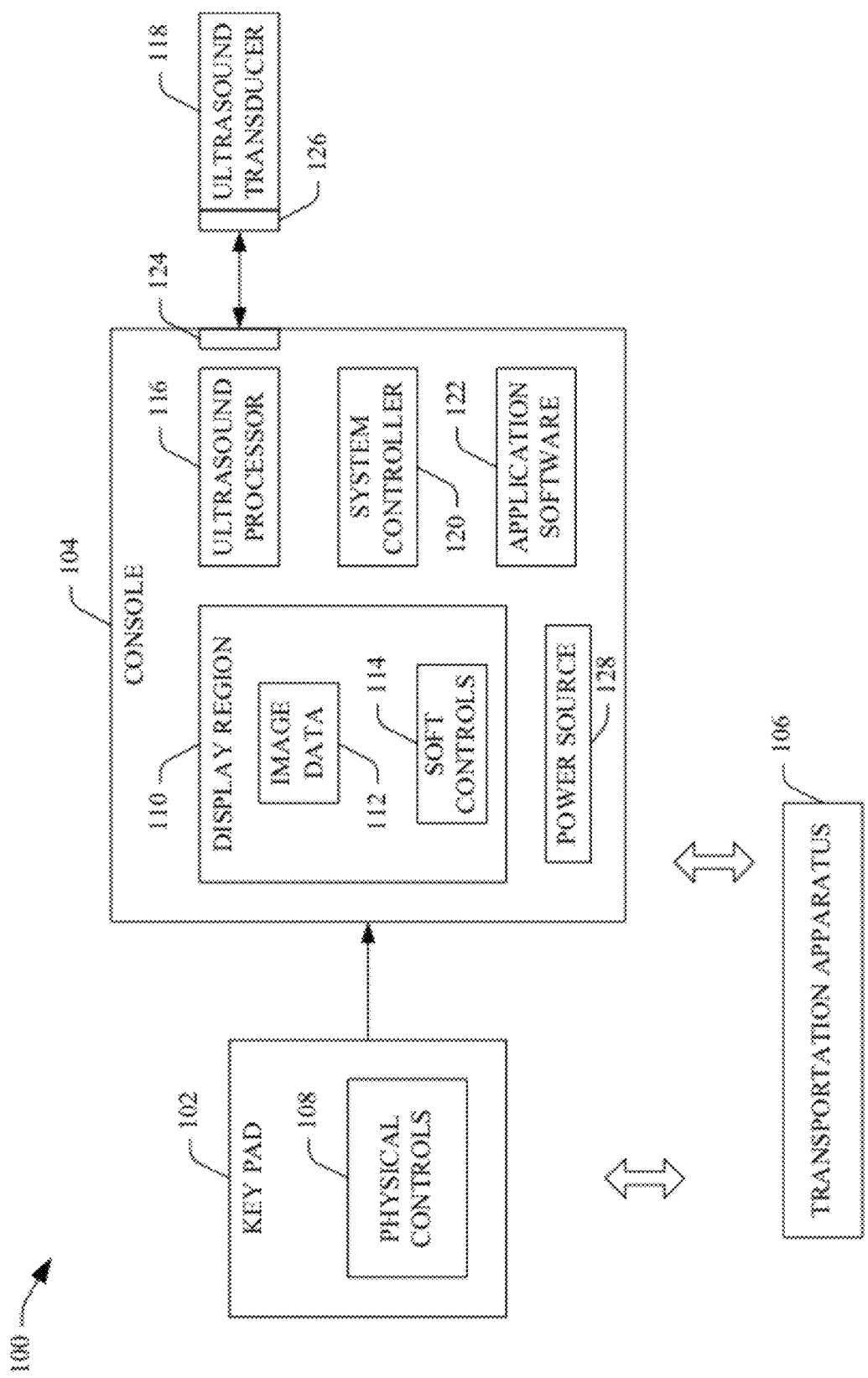
FIG. 1 illustrates an example ultrasound imaging system including a key pad and a console.

FIG. 1 illustrates an ultrasound imaging system 100, which includes a key pad 102, a console 104, and a transportation apparatus 106 to which the key pad 102 and the console 104 are affixed.

The key pad 102 includes a set of physical controls 108 configured to activate and/or control at least one imaging function of the ultrasound imaging system 100. In one non-limiting instance, the set of physical controls 108 make up a primary set of controls (which is a sub-set of the total number of controls), which include a set of controls that are generally used more often and/or frequently for performing imaging procedures than other controls.

As described in greater detail below, in one instance, the set of physical controls 108 includes less than ten, less than five, or other non-zero number of controls configured to activate at least one imaging function, which allows for a relatively narrow key pad 102, relative to a configuration in which the key pad 102 includes more controls. The set of physical controls 108 can also be configured such that they are part of a hermetically sealed surface of the key pad 102.

The console 104 includes a human readable display region 110, which is configured to concurrently display both image data 112 and a touch screen menu including a soft controls 114 configured to activate and/or control at least one imaging function. In one non-limiting instance, the set of soft controls 114 make up a secondary set of controls (which is another sub-set of the total number of controls), which include a set of controls that are generally used less often and/or frequently than the primary controls.

As described in greater detail below, the display region 110 is configured such that a spatial orientation of the image data 112 and the soft controls 114, with respect to each other, provides for narrow console footprint with a large image display and easily visualized and readily accessible soft controls 114. For example, in one instance, the set of soft controls 114 are visually presented concurrently with and below the image data 112 in the display region 110.

It is to be appreciated that the large image display facilitates viewing a relatively large distance like across a surgical bed, allows for presentation of details without loss of overview without zooming in, allows for display of two planes/views in near fill size, additional images or information like Doppler spectrums, 3D cubes, measurements, etc. A narrow footprint allows for using the system 100 in small rooms such as operating rooms, easily transporting the system 100 in hallways, crowded elevators, from room to room, etc.

The console 104 further includes an ultrasound processor 116 configured to interface with an ultrasounds transducer 118 that transmits ultrasound signals and receives echoes when utilized to perform an ultrasounds procedure. The ultrasound processor 116 generates, based on the received echoes, two dimensional (2D), three-dimensional (3D) or other ultrasound image data indicative of an object under examination.

A system controller 120 controls the console 104 including one or more components thereof based on application software 122 stored on physical memory thereof and/or accessible thereto. For example, the system controller 120 can control the console 104 such that the ultrasound image data is the image data 112 displayed in the display region 110. In another example, the system controller 120 can control the console 104 such that the soft controls 114 are based on one or more instructions of the application software 122.

The console 104 further includes an interface 124 configured to connect with a complementary interface 126 of the ultrasound transducer 118. The interfaces 124 and 126 include suitable pathways and/or connectors for conveying control and/or data signals between the console 104 and the transducer 118.

A suitable ultrasound transducer 118 includes a single element transducer or a multiple element transducer array, which captures information for two dimensional, three dimensional, four dimensional, Doppler, and/or other ultrasounds imaging modes. The interface 124 may be configured to alternately interface with other probes, for example, different frequency probes, probes with different capabilities, and/or other probes.

The transportation apparatus 106 includes wheels or the like. As such, the transportation apparatus 106 and hence the key pad 102, the console 104, and the ultrasound transducer 118 can be transported from one room to another room and/or within a room.

A power source 128 includes a power converter for converting power from an outside source such as a power cube, a power supply, an AC receptacle, or other power source for powering electrical components of the imaging system 100.

The power source 128 may additionally or alternatively include a primary (non-rechargeable) battery, a secondary (rechargeable) battery, a super capacitor, and/or the like that supplies power for one or more of the components of the imaging system.

FIGS. 2-5 illustrate various non-limiting examples of the display region 110 of the console 104 in connection with the key pad 102 and the physical controls 108. Initially referring to FIG. 2, the console 104 includes a monitor 200, such as a liquid crystal display (LCD), plasma, light emitting diode (LED), cathode ray tube (CRT), or other monitor, which is integrated in and is part of the console 104.

The display region 110 is two dimensional and includes a vertical dimension $V_{dr}$ and a horizontal dimension $H_{dr}$, which is less than the vertical dimension $V_{dr}$. Generally, this orientation can be considered as "portrait" in contrast to "landscape" in which the horizontal dimension is greater than the vertical dimension. A first or upper portion 202 of the display region 110 is configured to visually present the image data 112. In the illustrated embodiment, the portion 202 is generally quadratic in shape. A second or lower portion 204 is configured to visually present the soft controls 114.

This configuration of upper and lower portions 202 and 204 allows for a narrow footprint (with respect to the horizontal dimension of the system) with a large image display covering the horizontal footprint of the display region 110 with the soft controls 114 located just below the image data 112 such that the user can identify and employ the soft controls 114 without moving his/her eyes way from the image data. In addition, positioning the soft controls 114 as such shortens the distance between the image data 112 and the soft controls 114.

The key pad 102 is located below (with respect to the vertical dimension $V_{dr}$) the console 104 and has a width $W_{kp}$, which is less than a width $W_c$ of the console 104, and, thus, does not increase the footprint in the horizontal direction relative to the console 104. Note that the key pad 102 can be smaller relative to a configuration in which all of the controls are part of the key pad 102. In addition, the key pad 102 and lower portion 204 provide the feel as is one is an extension of the other or that they are part of the same set of controls.

FIG. 3 is substantially similar to FIG. 2 except that the soft controls 114 do not occupy the entire lower portion 204. In this example, a region 302 not occupied by the soft controls can be used to present other information or no information at all. Furthermore, the window of the soft controls may be moveable and/or scalable within the lower portion 204. Although not shown, this may also apply to the image data 112 and the upper portion 202. In this example, the key pad width $W_{kp}$ is about a same size as the console $W_c$. In another instance, $W_{kp}$ can be greater than $W_c$.

FIG. 4 shows another embodiment in which the upper portion 202 presents the soft controls 114 and the lower portion 204 presents the image data 112. FIG. 5 shows another embodiment in which one sub-portion of the soft controls 114 is located above the image data 112 and another sub-portion of the soft controls 114 is located below the image data 112. In another instance, the display region 110 is configured such that the user can variously position the image data 112 and/or the soft controls 104 within the display region 110.

Figure 6:
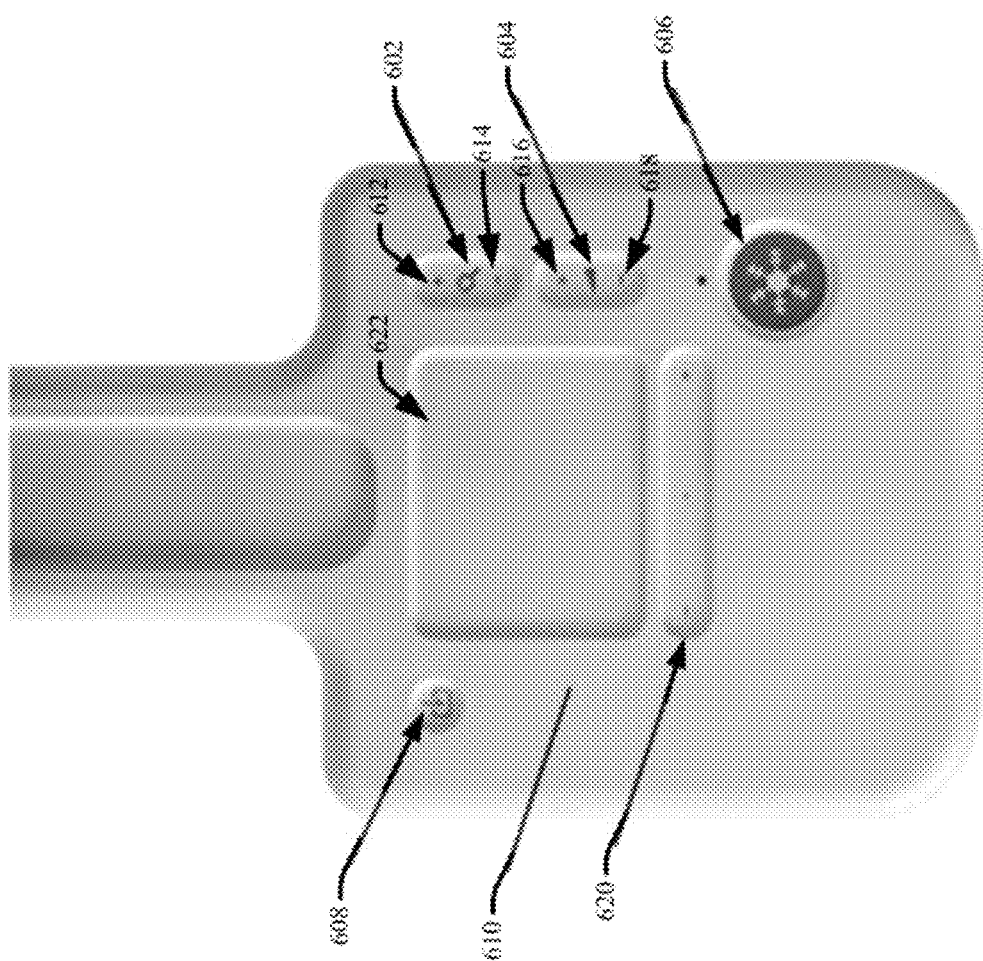
FIG. 6 illustrates an example of the key pad, including physical controls thereof.

FIG. 6 illustrates an example key pad 102 and physical controls 108.

In this example, the physical controls 108 includes four (4) function controls—a gain function control 604, a depth function control 602, a freeze function control 606, and a print/store function control 608. A region over each of the controls 602-608 includes a visual graphic or indicia representing the control. In the illustrated embodiment, the visual graphic or indicia are located in a recess in the surface 610. The visual graphic allows the user to easily visually identify a particular control offered through the key pad 102.

The gain function control 604 includes dedicated increase and decrease adjustors 616 and 618, and the depth function control 602 includes dedicated increase and decrease adjustors 612 and 614. A shared increase and decrease adjustor 620 can also be used to increase and decrease the gain and depth. The adjustor 620 can further be used to adjust a soft control 114, which is selected by hovering the screen cursor over a function of interest and/or otherwise.

The adjustors 612-620 respectively include proximity sensors (e.g., capacitive, magnetic, etc.) and/or touch sensitive areas located under or behind a surface 610 of the key pad 110. A region over each of the sensor includes a visual graphic or indicia representing the corresponding function (e.g., "+" or "−"). In the illustrated embodiment, the sensor indicia are located in the recess in the surface 610 (along with the control indicia). The sensor visual graphics allow the user to easily visually identify and employ a particular function for a control. The adjustors 612-620 can be actuated by bringing a finger close to the sensors, touching the sensors, and/or sliding the finger along the sensors in a recess.

A touch pad 622 is used to move a graphical cursor or pointer presented in the display region 110. Likewise, the touch pad 622 is located in a recess of and behind the surface 610.

In the illustrated embodiment, the surface 610 is sealed (e.g., hermetically). This facilitates preventing foreign matter such as bodily fluids, liquids, dirt, etc. from entering the key pad 102 through the surface 610 such as in connection with the various controls 602-608, adjustors 612-620 and touch pad 622. The sealed surface and the recesses in the surface 610 render the surface 610 easily cleanable. In one instance, this include disinfectable and/or sterlizeable.

In an alternative embodiment, the key pad 102 also includes one or more indicators such as a visual indicator (e.g., a light emitting diode (LED)), an audible indicator, etc. to provide feedback to an operator. Suitable feedback may relate to a currently activated function control, sensed touch, power status, etc.

It is to be understood that the set of controls illustrated in this example are provided for explanatory purposes and is not limiting. As such, in other embodiment, more, less the same and/or different controls may be part of the controls 108. Examples of other controls include, but are not limited to, controls for setting parameters, making measurements, controlling operation, selecting a scanning mode, initiate scanning, etc. One or more of these and/or other functions may additionally or alternatively be part of the set of soft controls 104.

Figure 9:
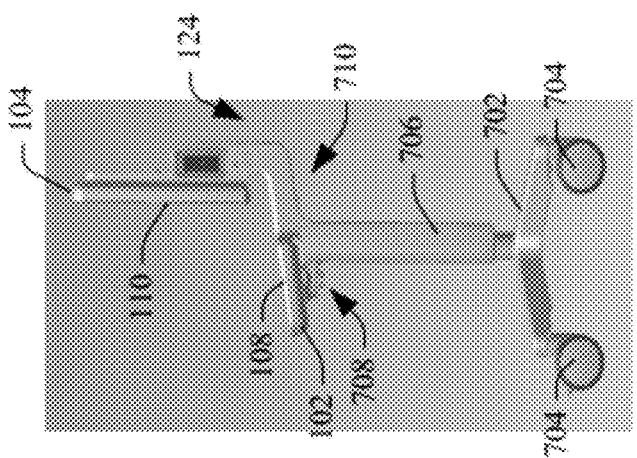
FIG. 9 illustrates a side view of an example of the ultrasound imaging system.
Figure 8:
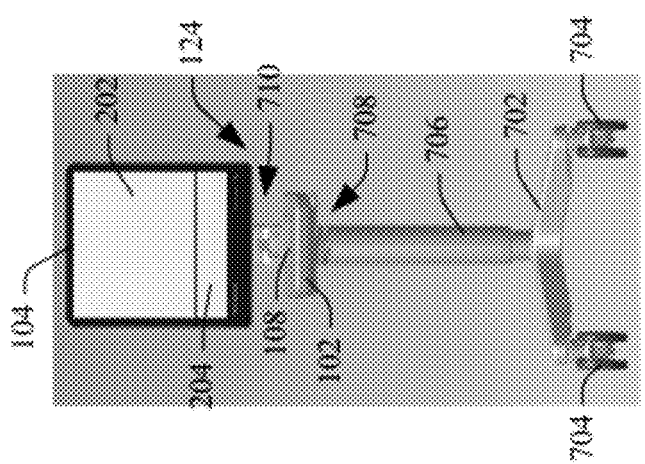
FIG. 8 illustrates a front view of an example of the ultrasound imaging system.
Figure 7:
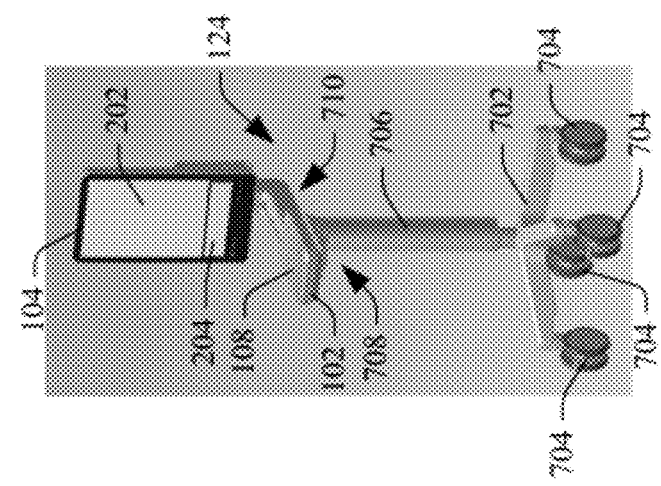
FIG. 7 illustrates a perspective view of an example of the ultrasound imaging system.

FIGS. 7-9 illustrate an example of the key pad 102 and the console 104 in connection with the transportation apparatus 106. FIG. 7 illustrates a perspective view, FIG. 8 illustrates a front view, and FIG. 9 illustrates a side view.

In this example, the transportation apparatus 106 includes a base portion 702 with four (4) or other desired number of wheels 704, which allow the imaging system 100 to be rolled from location to location such as operating room to operating room or other location. One end of a post 706 is affixed to the base portion and the other end of the post 706 includes a first region 708 to which the key pad 102 attaches and a second region 710 to which the console 104 attaches. The post 708 may be a fixed height or include a telescoping or otherwise height adjustable member, which can be used to adjust the height of the key pad 102 and the console 104.

In the illustrated embodiment, the console 104 attaches to the second region 710 such that the surface of the display region 110 and upper and lower regions 202 and 204 is generally perpendicular to the floor. The key pad 102 attaches to the first region 708 such that the key pad runs at a slight angle downward horizontally from the console 104 from just below the display region 110 away from the console 104. In one instance, the relative position of the key pad 102 and/or the console 104 is adjustable in that they can pivot, rotate and/or translate.

In another embodiment, the key pad 102 and/or the console 104 are removeably affixed to the transportation apparatus 124 or affixed to another apparatus such as a generally stationary apparatus mounted to a floor, wall, ceiling and/or the like. In the illustrated embodiment, the console 104 includes an LCD monitor. In another embodiment, the console 104 can include a plasma, CRT, or other monitor.

Figure 10:
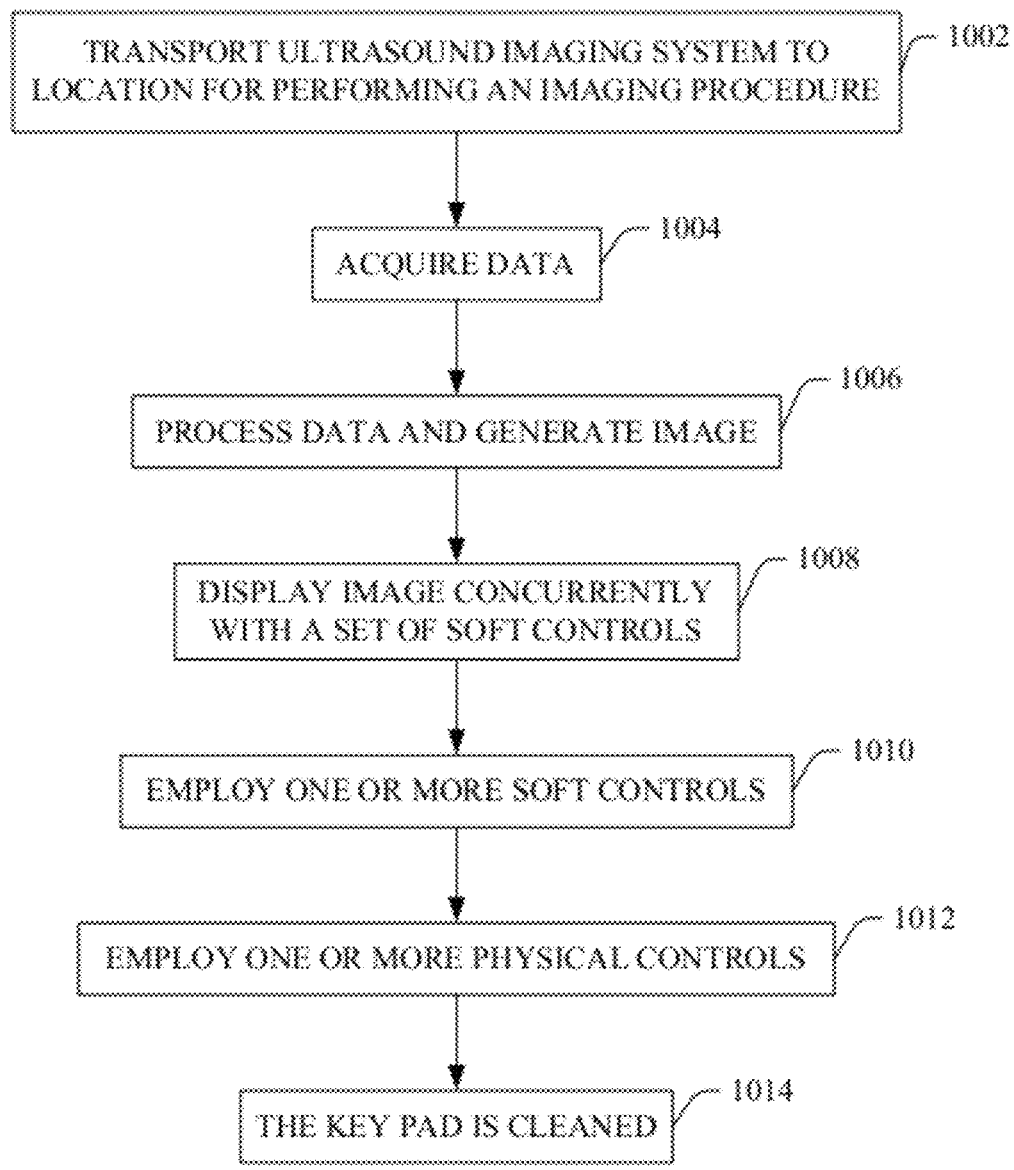
FIG. 10 illustrates an example method for using the ultrasound imaging system.

FIG. 10 illustrates an example method for employing the imaging system 100.

It is to be understood that the following acts are provided for explanatory purposes and are not limiting. As such, one or more of the acts may be omitted, one or more acts may be added, one or more acts may occur in a different order (including simultaneously with another act), etc.

At 1002, an ultrasound imaging system is transported to a location for performing an imaging procedure. As discussed herein, the narrow footprint of the key pad 102 and the console 104 allows the system 100 to be used in areas with limited space such as an operating room.

At 1004, ultrasound data is acquired.

At 1006, the ultrasound data is processed, generating at least one image.

At 1008, the image is presented in a display region concurrently with a set of soft controls. As described herein, the display orientation can be a portrait orientation as shown FIG. 2 and/or other figures, which allows for display of a large image in an upper portion 202 of the display region 110 and the soft controls in a lower portion 202 of the display portion 110, which is below the upper portion 202.

At 1010, optionally, one or more of the soft controls are employed to invoke one or more secondary ultrasound imaging functions.

At 1012, optionally, one or more physical controls 108 of the key pad 102 are employed to invoke one or more primary ultrasound imaging functions. As described herein, the physical controls 108 on the key pad 102 provide extremely simple and fast access to primary functions.

At 1014, after the imaging procedure, the key pad 102 is cleaned. As discussed herein, the fully sealed surface with the controls 108 is easily cleaned.

The application has been described with reference to various embodiments. Modifications and alterations will occur to others upon reading the application. It is intended that the invention be construed as including all such modifications and alterations, including insofar as they come within the scope of the appended claims and the equivalents thereof.

What is claimed is:

1. An ultrasound imaging system, comprising:
   an ultrasound transducer;
   a console, including:
      an ultrasound processor that processes ultrasound data acquired by the ultrasound transducer; and
      a monitor with a two dimensional display region having a vertical dimension and a horizontal dimension, wherein the horizontal dimension is smaller than the vertical dimension, and the display region includes an upper portion configured to display image data and a lower portion configured to display, concurrently with displaying the image data in the upper portion, a touch screen menu including a set of soft controls that are respectively configured to control a secondary set of ultrasound imaging functions; and a key pad including a set of physical controls that are respectively configured to control a primary set of ultrasound imaging functions, wherein the key pad has a width that is less than a width of the console, wherein the console and the key pad are part of different units of the ultrasound imaging system, wherein the key pad includes only four functions controls, including a gain function control, a depth function control, a freeze function control and a print/store function control, and an adjustor which alternatively adjusts a depth and a gain of an active one of the depth function control and the gain function control, and wherein the four functions controls and the adjustor are located in respective recesses within a surface of the key pad and are marked with identification and activation graphical indicia.

2. The system of claim 1, wherein the key pad includes a touch pad configured to move a graphical cursor displayed on the monitor.

3. The system of claim 1, wherein the common adjustor alternately controls the depth, the gain and a function of a soft control of the set of soft controls of the touch screen menu.

4. The system of claim 1, further comprising:
a transportation apparatus, wherein at least one of the console or the key pad are removeably affixed to the transportation apparatus.

5. The system of claim 1, further comprising:
a stationary apparatus mounted to at least one of a floor, a wall or a ceiling, wherein at least one of the console or the key pad are affixed to the stationary apparatus.

6. The system of claim 1, the key pad, further comprising:
a hermetically sealed surface that includes regions for activating the set of physical controls.

7. The system of claim 6, wherein the hermetically sealed surface includes at least one non-recessed portion and recessed portions, which are recessed relative to the non-recessed portion, and the regions are part of the recessed portions of the hermetically sealed surface.

8. The system of claim 7, further including touch sensitive areas that sense tactition of the recessed regions and generate a signal indicative thereof.

9. The system of claim 6, wherein the hermetically sealed surface is at least one of disinfectable or sterilizeable.

10. The system of claim 1, wherein the display region is part of a single monitor that is integrated in and part of the console.

11. The system of claim 1, wherein the display region is configured in a portrait orientation.

12. The system of claim 1, further comprising:
an ultrasound transducer, including a communications interface, and the console, further comprising: a complementary communications interface, which is complementary to the communications interface of the ultrasound transducer, wherein the console and the ultrasound transducer communicate via the communications interface and the complementary communications interface; and a transportation apparatus having at least one wheel, wherein the console is affixed to the apparatus and the key pad is affixed to the transportation apparatus, and the console and the key pad are independent devices in different housings.

13. An ultrasound imaging system, comprising:
a console with a display region arranged in a portrait orientation, wherein the display region includes at least a first portion and a second different portion, and concurrently presents ultrasound image data generated by the system in the first portion of the display region and a set of soft secondary ultrasound imaging controls in the second different portion of the display region;

a key pad including a set of primary ultrasound imaging controls, wherein each of primary ultrasound imaging controls are touch sensitive areas located in a respective recesses in a surface of the key pad behind the surface, wherein the keypad further includes at least one of a visual light indicator or an audible indicator, and wherein the console and the key pad are not part of a same component of the ultrasound imaging system; and an ultrasound transducer interface that electrically communicates with a complementary interface of an ultrasound transducer in response to the ultrasound transducer being installed with the ultrasound imaging system.

14. The system of claim 13, wherein the set of primary ultrasound imaging controls includes four or less controls configured to control different ultrasound imaging functions.

15. The system of claim 14, wherein the set of primary ultrasound imaging controls is part of a hermetically sealed surface of the key pad.

16. The system of claim 15, wherein the set of primary ultrasound imaging controls control at least one of gain, depth, freeze or print/store functions.

17. The system of claim 16, wherein a width of the key pad is narrower than a width of the display region.

18. A method, comprising:
concurrently displaying ultrasound image data and a set of soft controls vertically with respect to each other in a same display region of a console of an ultrasound imaging system, wherein a set of physical controls are part of a key pad of the ultrasound imaging system, which is narrower than the console of the ultrasound imaging system and is part of a separate unit of the ultrasound imaging system, wherein the console and the keypad are removeably affixed to a transportation apparatus.

19. The method of claim 18, wherein the set of physical controls includes four or less controls configured to control different ultrasound imaging functions.

20. The method of claim 18, wherein the set of physical controls is part of a hermetically sealed surface of the key pad.

21. The method of claim 18, further comprising:
receiving an input indicative of a user selected one of the soft controls; and
invoking a corresponding ultrasound imaging function in response to receiving the input.

22. The method of claim 18, further comprising:
receiving an input indicative of a user selected one of the physical controls; and
invoking a corresponding ultrasound imaging function in response to receiving the input.

* * * * *